(12) United States Patent
Asahara et al.

(10) Patent No.: US 7,867,230 B2
(45) Date of Patent: Jan. 11, 2011

(54) BIPOLAR FORCEPS

(75) Inventors: Tomohiko Asahara, Shiga (JP); Takeshi Mikami, Hokkaido (JP); Kiyohiro Houkin, Hokkaido (JP)

(73) Assignee: Johnson & Johnson Kabushiki Kaisha, Tokyo (JP)

( * ) Notice: Subject to any disclaimer, the term of this patent is extended or adjusted under 35 U.S.C. 154(b) by 875 days.

(21) Appl. No.: 11/278,622

(22) Filed: Apr. 4, 2006

(65) Prior Publication Data

US 2006/0276785 A1 Dec. 7, 2006

(30) Foreign Application Priority Data

Apr. 5, 2005 (JP) ............... 2005-109055

(51) Int. Cl.
*A61B 18/14* (2006.01)

(52) U.S. Cl. ...................................... 606/51

(58) Field of Classification Search ............. 606/41–52
See application file for complete search history.

(56) References Cited

U.S. PATENT DOCUMENTS 4,302,374 A * 11/1981 Helle et al. ................. 524/168
5,197,962 A  3/1993 Sansom
7,160,297 B2 * 1/2007 Nesbitt ....................... 606/45
2003/0163125 A1 8/2003 Greep
2003/0171748 A1 9/2003 Truckai

FOREIGN PATENT DOCUMENTS

JP          7275255 A    10/1995
JP         11335859 A    12/1999

OTHER PUBLICATIONS

Ceviker, N., et al: "A New Coated Bipolar Coagulator: Technical Note": ACTA Neurochirurigica; 1998; pp. 619-620; vol. 140; Austria.

* cited by examiner

*Primary Examiner*—Lee S Cohen

(57) ABSTRACT

This invention provides bipolar forceps that are used for coagulation, dissection or similar surgical manipulation by the application of a high-frequency current in a surgical operation, which suppresses attachment and sticking of burned protein to arm tip end portions irrespective of the properties of the metal material forming the arms. The bipolar forceps according to the present invention have on each of opposed surfaces 1*a* of the tip end portions 1 of a pair of arms a composite plating film 3 composed of a noble metal material 3*a* and nonconductive fine particles 3*b*, and a laminate plating film 4 of a noble metal material formed on the composite plating film 3.

5 Claims, 2 Drawing Sheets

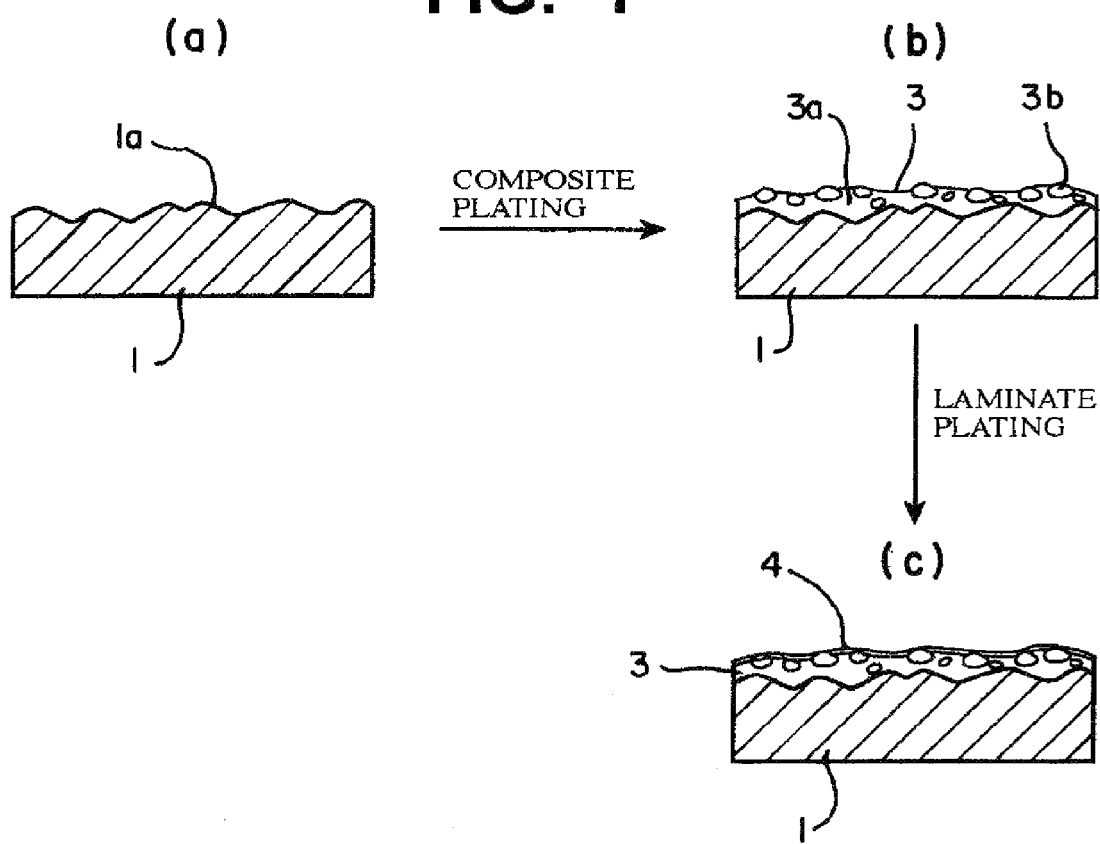

BIPOLAR FORCEPS

BACKGROUND OF THE INVENTION

Field of the Invention

The present invention relates to bipolar forceps for coagulation, hemostasis, dissection or similar surgical manipulation of bodily tissue, mainly in vascular, plastic and general surgical operations.

In general, a pair of bipolar forceps is a surgical instrument provided with a pair of opposed arms connected to a high frequency generator, electrically insulated from each other, and adapted to be openable and closable at their tip end portions. Normally, when a surgeon is not manipulating (while not in use), the arms are in their open state with the opposed surfaces of their tip end portions held apart, whereas in use when a surgeon is manipulating the arms are in their closed state with the opposed surfaces of their tip end portions in contact with each other with a bodily tissue clamped therebetween so that the application of a high-frequency current across the opposed surfaces permits easy coagulation on bodily tissue or similar surgical manipulation.

Conventionally the arms of such bipolar forceps are made of stainless steel, a titanium alloy, or silver alloy, and in recent years there are known forceps of the type that at least opposed surfaces of the arm tip end portions are plated with a noble metal (see Japanese Patent Application Publication No. 7-275255 (1995), for instance).

With such known bipolar forceps, a high-frequency current is applied across the opposed surfaces of the tip end portions for coagulation, hemostasis, dissection or similar surgical manipulation as described above, and in this case the current needs to be large to some extent to ensure accomplishment of the intended surgical manipulation. Naturally enough, a decomposition product of protein, which results from heat generation by the current application, attaches to and gets burnt on the opposed surfaces of the tip end portions of the arms. It is well-known in the art that the decomposition product of protein on the opposed surfaces of the tip end portions lessens the effect of coagulation, hemostasis or the like in the surgical operation. This is a frequent phenomenon with forceps made of stainless steel or titanium alloy of relatively low thermal or electrical conductivity. With such forceps, the more the high-frequency current is increased to carry out a quick and accurate surgical operation, the more protein becomes attached or sticks to (getting burnt on) the opposed surfaces of the tip end portions of the arms, necessitating interruption of coagulation, hemostasis, dissection or similar surgical manipulation to wipe or wash off the deposited decomposition product of protein.

As a solution to this problem there is proposed such a method as shown in FIGS. 2(a) and 2(b), according to which each opposed surface 1a of each tip end portion 1 is plated, by bright dipping, with a noble-metal plated film 2 excellent in thermal and electrical conductivity and having as much flattened or smoothed a surface as possible to provide microscopic current density on the tip end portion 1 of each arm to thereby prevent temperature variations. This method is effective to some extent in that providing the noble-metal plated film 2 is an easy method to improve the corrosiveness and conductivity of the arms that derive from the properties of the metal material that constitutes the arms. However, the noble-metal plated film 2 is not effective enough to suppress the deposition of protein on the tip end portion 1, and for this reason, the proposed method is not a complete solution to the problem mentioned above.

SUMMARY OF THE INVENTION

An object of the present invention is to provide a pair of bipolar forceps which is used for coagulation, dissection, or similar surgical manipulation through application of a high-frequency current in a surgical operation and which suppresses the deposition or adherence of protein to the tip end portions of arms irrespective of the properties of the metal material forming the arms.

The invention of this application is a pair of bipolar forceps provided with a pair of closable arms which are normally spaced apart at one end and insulated from each other and, when in use, held in contact with each other and supplied with a high-frequency current, wherein opposed surfaces of tip end portions of said pair of arms are each coated with a composite plating film of a noble metal material and nonconductive fine particles, and a laminate plating film of a noble metal material formed on said composite plating film.

According to the invention of this application, said noble metal material is at least one kind of metal selected from a group consisting of gold, platinum, silver, palladium, nickel, chromium, copper and tin.

According to the invention of this application, said nonconductive fine particles consist of a polytetrafluoroethylene or fluorinated ethylene polymer.

According to the invention of this application, the content of said nonconductive fine particles in said composite plating film is in the range of 0.05 wt % to 20.0 wt %.

According to the invention of this application, the content of said nonconductive fine particles in said composite plating film is in the range of 4 percent by volume to 50 percent by volume.

According to the invention of this application, the thickness of said composite plating film is in the range of 3 μm to 50 μm, and the thickness of said laminate plating film is in the range of 0.2 μm to 10 μm.

According to the invention of this application, said fine particles range in particle size from 0.5 μm to 10 μm.

According to the present invention, since the composite plating films consisting of a noble metal material and nonconductive fine particles are coated on the opposed surfaces of the arm tip end portions, the opposed surfaces can be provided with roughness which reduces their contact areas with a bodily tissue, thereby suppressing the deposition and adhesion of protein to the tip end portions irrespective of the properties of the metal material used for the arms. This eliminates the necessity for interrupting the coagulation, hemostasis, dissection or similar surgical manipulation during surgical operation to wipe or wash off the decomposition product of protein as is required in the case of using the conventional bipolar forceps; hence, the bipolar forceps of the present invention are excellent in cleanliness, highly operable and ensure a smooth surgical operation without degrading the surgical manipulation performance, permitting reduction of the operation time. Furthermore, according to the present invention, since the above-mentioned composite plating film is covered with the laminate plating film consisting of a noble metal material, it is possible to prevent the nonconductive fine particles from dropping off the composite plating film and to maintain the surface roughness of each of the opposed surfaces provided by the composite plating film.

According to another aspect of the present invention, since the above-mentioned noble metal material is at least one kind of metal selected from a group consisting of gold, platinum, silver, palladium, nickel, chromium, copper and tin, the original manipulation performance of the bipolar forceps can be maintained by excellent thermal conductivity and electrical conductivity of the selected noble metal material.

According to another aspect of the present invention, since the above-mentioned nonconductive fine particles consist of a polytetrafluoroethylene or fluorinated ethylene polymer, the thermal and the electrical nonconductivity of the fluorine-series polymer increases the surface areas contacting the opposed surfaces of the arm tip end portions and, at the same time, decreases the areas of contact with the bodily tissue, suppressing the deposition and adhesion of protein to the arm tip end portions.

According to another aspect of the present invention, since the content of nonconductive fine particles in the above-mentioned composite plating film is set in the range from 0.05 wt % to 20.0 wt %, it is possible to provide, within this range, the opposed surfaces of the arm tip end portions with surface roughness suitable for suppressing the deposition and adhesion of protein to the arm tip end portions.

According to another aspect of the present invention, since the content of nonconductive fine particles in the above-mentioned composite plating film is set in the range from 4 percent by volume to 50 percent by volume, it is possible to provide, within this range, the opposed surfaces of the arm tip end portions with surface roughness suitable for suppressing the deposition and adhesion of protein to the arm tip end portions.

According to another aspect of the present invention, since the thickness of the above-mentioned composite plating film is set in the range from 3 μm to 50 μm, and the thickness of the above-mentioned laminate plating film is set in the range from 0.2 μm to 10 μm, it is possible to provide, within these ranges, the opposed surfaces with surface roughness which reduces their areas of contact with the bodily tissue, ensuring the original manipulation performance of the bipolar forceps and prevention of the nonconductive fine particles from dropping off the composite plating film, thereby maintaining the above-mentioned surface roughness of the opposed surfaces of the arm tip end portions.

According to another aspect of the present invention, since the fine particles ranges in particle size from 0.5 μm to 10 μm, it is possible to provide, within this range, the opposed surfaces of the arm tip end portions with surface roughness which reduces their areas of contact with the bodily tissue, thereby ensuring the original manipulation performance of the bipolar forceps.

BRIEF DESCRIPTION OF THE DRAWINGS

FIG. 1 is a sectional diagram showing the surface treatment process of opposed surfaces of arm tip end portions of the bipolar forceps according to an embodiment of the present invention, (a) showing the state prior to the surface treatment, (b) showing the state after the formation of the composite plating film over the surface of each opposed surface, and (c) showing the state after completion of the surface treatment by forming the laminate plating film on the surface the composite plating film.

DETAILED DESCRIPTION OF THE PREFERRED EMBODIMENTS

The present invention will hereinafter be described in detail.

The inventors of this invention had earnestly studied conventional bipolar forceps to find out how to suppress sticking of burned protein to their tip end portions; and they have discovered that it is possible to suppress the deposition of the decomposition product of protein and hence suppress its sticking (burning on) to the opposed surfaces of the arm tip end portions by roughening them, rather than tendency of development toward ultra-smoothing of opposing surfaces by noble metal plated films formed on the conventional bipolar forceps. In addition, they have clarified for the first time that the deposition or adhesion of protein can be prevented not only by roughening the opposed surfaces of the arm tip end portions, but also by forming the laminate plating film as a protective film on each roughened surface.

Embodiment 1

Figure 3:
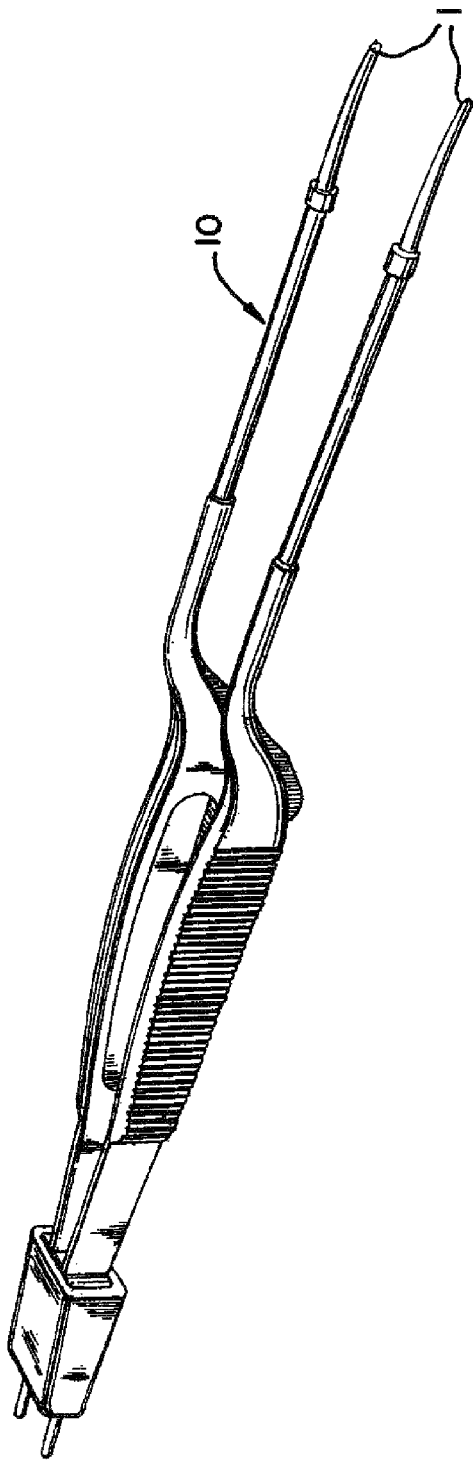
FIG. 3 is a perspective view of a pair of bipolar forceps.
Figure 2:
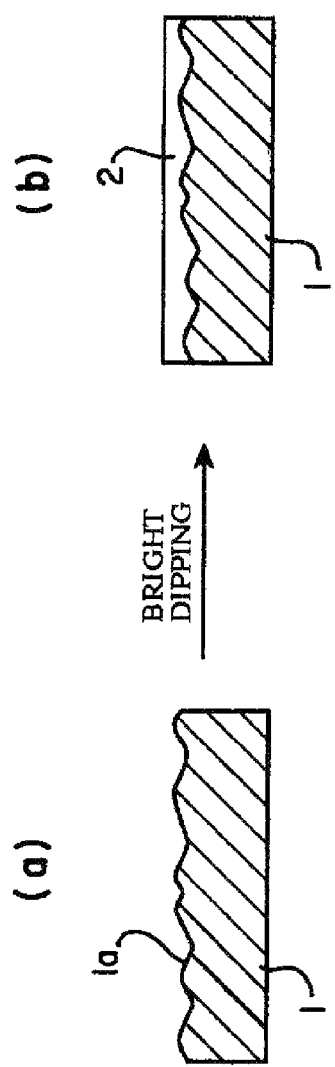
FIG. 2 diagrammatically shows in section the surface treatment process of opposed surfaces of arms tip end portions of a conventional bipolar forceps, (a) showing the state prior to the surface treatment, and (b) showing the state after the surface treatment.

The bipolar forceps 10 of an embodiment according to the present invention is based on the above-mentioned findings, as illustrated in FIG. 3. On each of opposed surfaces 1a of arm tip end portions 1 of the bipolar forceps shown in FIG. 1(a) there is formed, by plating, a composite film 3 that forms a roughened surface on each of the opposed surfaces 1a as shown in FIG. 1(b). The composite plating film 3 is formed principally of a noble metal material 3a, nonconductive fine particles 3b and a dispersing agent (not shown).

Selected as the noble metal material 3a is a material that is excellent in electrical and thermal conductivity and excellent in biocompatibility as well, and it may preferably be selected, for example, from a group consisting of gold, platinum, silver, palladium, nickel, chromium, copper and tin, but other materials, such as noble metals (group 10 element) and their sub-species (group 11 element) are also electrochemically stable and can similarly be used.

Selected as the nonconductive fine particles 3b is a material that is less electrically and thermally conductive and excellent in biocompatibility, such as polytetrafluoroethylene (hereinafter referred to as PTFE), fluorinated ethylene polymer, or similar fluorine series polymer; in particular, polytetrafluoroethylene is preferable. The fine particles of such a fluorine series polymer are contained as the nonconductive fine particles 3b in the composite plating film 3, and held in the noble metal material 3a to form asperities on the surface of the film 3, hence contributing to roughening of the film surface.

The mixture ratio of the fine particles consisting of such a fluorine series polymer to the composite plating film 3 is limited to a certain range that is appropriate from the viewpoints of metal plating stability and film stability. With too small an amount of nonconductive fine particles 3b added, surface roughening of each of the opposed surfaces 1a is insufficient; for example, in the case of using a metal of high specific gravity, such as gold, the amount of nonconductive fine particles 3b needs to be at least 0.05 wt %. On the other hand, when the amount of nonconductive fine particle 3b is too large, too many nonconductive fine particles 3b protrude from the surface of the composite plating film 3, and for this reason, the amount of fine particles needs to be smaller than 20 wt %. Accordingly, the amount of fine particles may preferably be set in the range from 4 percent by volume to 50 percent by volume.

There is an appropriate range for the particle size of the nonconductive fine particles 3b consisting of the fluorine series polymer to be contained in the composite plating film 3; the average particle size is required to range from 0.5 µm to 10 µm. When their average particle size is smaller than 0.5 µm, the fine particles are practically associated and the actual particle size is not small, whereas when the average particle size exceeds 10 µm, the nonconductive fine particles 3b constitute an obstacle to the formation of a stable film. In general, it is practical that the average particle size be in the range of 3 µm to 6 µm, and this range may preferably be used. The thickness of the composite plate film 3 corresponding to the above-mentioned range of the average particle size is required to be in the range of 3 µm or more to 50 µm or less when the amount of nonconductive fine particles 3b is small.

The dispersing agent is a component that is added to disperse the nonconductive fine particles 3b uniformly throughout the noble metal material 3a to thereby provide uniform surface roughness on the entire surface of the composite plating film 3.

Furthermore, the composite plating film 3 of the bipolar forceps is covered, as depicted in FIG. 1(c), with a laminate plating film 4 that maintains and protects the surface roughness of the composite plating film 3. The laminate plating film 4 is formed of the above-mentioned noble metal material, and this material may be the same as or different from the noble metal material 3a forming part of the composite plating film 3. The use of the same noble metal material for the composite plating film 3 and the laminate plating film 4 could provide a merit in material acquisition for manufacture, but even if different materials are used, no particular problem arises in the maintaining the original manipulation performance of the bipolar forceps. In other words, the noble metal materials are all low in ionization tendency and they do not greatly differ in the ionization tendency; hence, even if different noble metals are contained in the two films, they are electrochemically stable when the forceps are actually used in a living body, providing biocompatibility.

When the surface roughness of the composite plating film 3 is large, the laminate plating film 4 needs to be formed 10 µm thick to protect the nonconductive fine particles 3b contained in the composite plating film 3, but when the surface roughness of the composite plating film 3 is small, a very small thickness of approximately 0.2 µm will suffice. That is, it is necessary that the thickness of the laminate plating film 3 be in the range of 0.2 µm to 10 µm.

As described above, in Embodiment 1 the surface of each opposed surface 1a, formed by plating the noble metal/nonconductive fine particle composite plating film 3 with the laminate plating film 4 consisting of a noble metal material, is appreciably uneven rough surface as shown in FIG. 1(c). It is unexpected from the conventional bipolar forceps that amount of protein sticking to the surface of such large roughness is far smaller than in the case of the conventional metal plated film which has a smooth surface of small roughness, but the inventors have arrived at the present invention by proving this finding. In other words, in the case of ordinary average bipolar forceps made of stainless steel, the surface roughness Ra of the arm tip end portion ranges from 0.15 µm to 0.30 µm, and in the case of bipolar forceps having gold-plated ultra-smooth surfaces, Ra ranges from 0.03 µm to 0.05 µm, whereas in the case of the bipolar forceps of Embodiment 1 the surface roughness Ra ranges from 0.10 µm to 0.30 µm substantially the same as that of the stainless-steel bipolar forceps in which protein gets burnt on the arm tip end portions in large quantities, but the forceps of this embodiment remarkably suppresses deposition of protein.

The present invention will be described below in detail with reference to its examples.

The amounts of decomposition products of burned protein sticking to arm tip end portions of a plurality of bipolar forceps are evaluated qualitatively and quantitatively by the evaluation method proposed by Mikami and others, the inventors of this application, and described in J. Neurosurg: Vol. 100, pace 133-138, 2004. That is, bipolar forceps whose opposed tip end portions are identical in shape and size (all of which are 1.00 mm wide in the examples) are used, with 100-µL (microliter) whole blood of a human applied on the tip end portions. The opposed tip end portions are spaced 1.0 mm apart, and the same high-frequency output (high-frequency generator (Malis (trademark), Generator, 15 Malis Unit, 1.6 W) is applied across the opposed tip end portions to coagulate the whole blood. Then, the coagulated blood sticking to the tip end portions is subjected to ultrasonic cleaning under the same condition, and the amounts of protein in the coagulated blood still remaining on the tip end portions are determined. The adhesion of how firm the protein is attached to the tip end portions is assessed in terms of the time necessary for removing by ultrasonic cleaning (2 W) the whole blood coagulated by the above-mentioned high-frequency generator for 20 seconds.

Such a quantitative method was used to compare the performance of the bipolar forceps (Example 1) according to the present invention with the performance of general products (comparative examples 1, 2 and 3).

Example 1

Bipolar forceps made of stainless steel and having arm tip end portions 1.0 mm wide were prepared, and the opposed surfaces of the arm tip end portions were each coated with a composite plating film (of a 4.3-µm thickness: measured with a test piece plated in the same bath) composed of pure gold and PTFE fine particles having an average particle size of 5 µm. The content of fine particles in the composite plating film was 1.05 wt % (or 7.87 percent by volume) and the surface roughness was Ra=0.199 µm. The composite plating film was coated with a pure-gold laminate plating film (of a 0.80-µm thickness: measured with a test piece plated in the same bath). The surface roughness of the laminate plating film was Ra=0.178 µm. With bipolar forceps so fabricated, the high-frequency generator used was 15 Malis Unit (1.6 W), the time for coagulation was 24 seconds, the opposed surfaces of the arm tip end portions were spaced 1.0 mm apart, and the amount of protein sticking to each opposed surface was determined by averaging the amounts of protein measured in five rounds of tests. With respect to the adhesion of protein, time required for removing protein by ultrasonic cleaning with Malis Power 17 (2 W) was measured, and the protein removing time was also determined by averaging those measured in five rounds of tests. The results are given in Table 1.

Comparative Example 1

The amounts of protein deposited on and its adhesion to the tip end portions of the stainless-steel bipolar forceps of Example 1 were assessed in the same manner as in Example 1 except that the tip end portions were not subjected to any surface treatment by plating, and the number of times of bumping was counted. The results are given in Table 1.

Comparative Example 2

The amounts of protein deposited on and its adhesion to each arm tip end portion of titanium-alloy bipolar forceps were assessed in the same manner as in Example 1 except that the tip end portions were not subjected to any surface treatment by plating, and the number of times of bumping was counted. The results are given in Table 1.

Comparative Example 3

The amount of protein deposited on and its adhesion to each arm tip end portion of the stainless-steel bipolar forceps of Example 1 were assessed in the same manner as in Example 1 except that the tip end portion was coated with an ultra-smooth gold-plated film by bright dipping, and the number of times of bumping was counted. The results are given in Table 1.

TABLE 1

|  | Amount of Protein Deposited | Protein Adhesion | Number of times of Bumping |
|---|---|---|---|
| Example 1 | AA | AA | 1 |
| Comparative Example 1 | D | C | 12 |
| Comparative Example 2 | C | D | 15 |
| Comparative Example 3 | B | A | 8 |

In Table 1, the amount of protein deposited was rated on a scale of 5 grades from AA (minimum) to D (maximum), and the adhesion of protein was rated on a scale of 5 grades from AA (most removable) to D (least removable). The number of times of bumping was determined by counting how many times bumping occurred in ten rounds of test in which 100-μL (microliter) whole blood of a human was placed on a glass plate and a high-frequency current was applied by Malis Unit 20. The firmer the adhesion of protein, a uniform current flow throughout the tip end portions becomes more difficult, resulting in the phenomenon of bumping.

As is evident from Table 1, comparison of the bipolar forceps using different materials for the arm tip end portions (Example 1, comparative examples 1 to 3) reveals that the characteristics of the bipolar forceps having the arm tip end portions according to the present invention (Example 1) significantly excel the characteristics of the other bipolar forceps (comparative examples 1 to 3). That is, the amount of protein deposited is far smaller than in the case of the stainless steel bipolar forceps having the same surface roughness as that in the present invention, and the adhesion of protein is smaller than in the case of the smooth gold-plated film surface. As a result, in the bipolar forceps (Example 1) the amount of protein deposited is markedly small and the adhesion of protein is also appreciably low; on either score, a significant difference, at $p<0.05$, was recognized between the forceps of the present invention and the conventional products (comparative examples 1 to 3).

Next, in addition to Example 1 and comparative examples 1 to 3, the amount of protein deposited and the adhesion of protein were rated quantitatively on the following Examples 2 to 4 using different noble metal materials.

Example 2

Nickel was used as a substitute for gold used as the noble metal material in Example 1, and PTFE fine particles having an average particle size of 5 μm were mixed with the nickel. The mixture was used to form the composite plating film. In the composite plating film, the amount of fine particles added was 15.2 wt % (or 22.8 percent by volume) and the film thickness was 10.4 μm; these values were measured with a test piece plated in the same bath. Then a laminate platinum-plated film was formed on the composite plating film. The thickness of the laminate plating film, measured with a test piece plated in the same bath, was 2.2 μm. The amount of protein deposited on the laminate plating film, similarly measured, was 1.4 mg, and the deposited-protein removing time, which indicates the adhesion of protein, was 6 seconds. Significant difference was recognized at $p<0.05$, between this example and any of comparative examples 2, 3 and 4.

Example 3

Platinum was used as a substitute for gold used as the noble metal material in Example 1, and the PTFE fine particles having an average particle size of 5 μm, as in Example 2, were mixed with the platinum. The mixture was used to form the composite plating film. In the composite plating film, the amount of fine particles added was 1.38 wt % (or 12.3 percent by volume) and the film thickness was 5.03 μm; these values were measured with a test piece plated in the same bath. A laminate gold-plated film was formed on the composite plating film. The thickness of the laminate plating film was 0.2 μm. The amount of protein deposited on the laminate plating film, similarly measured, was 1.2 mg, and the deposited-protein removing time, which indicates the adhesion of protein, was 4 seconds.

Example 4

Nickel was used as a substitute for platinum used as the noble metal material in Example 3, and PTFE fine particles having an average particle size of approximately 6 μm were mixed with the nickel. The mixture was used to form the composite plating film. In the composite plating film, the amount of fine particles added was 5.4 wt % (or 16.8 percent by volume) and the film thickness was 13.6 μm; these values were measured with a test piece plated in the same bath. A laminate tin-plated film was formed on the composite plating film. The amount of protein deposited on the laminate plating film, similarly measured, was 1.1 mg, and the deposited-protein removing time, which indicates the adhesion of protein, was 5 seconds.

TABLE 2

|  | Amount of Protein Deposited (in mg) | Adhesion of Protein (Removing Time in second) |
|---|---|---|
| Example 1 | 1.2 | 5 |
| Example 2 | 1.4 | 6 |
| Example 3 | 1.2 | 4 |
| Example 4 | 1.1 | 5 |
| Comparative Example 1 | 2.5 | 23 |
| Comparative Example 2 | 2.6 | 16 |
| Comparative Example 3 | 1.8 | 9 |

From Table 2 it is apparent that Examples 1 to 4 are all smaller in the amount of protein deposited and shorter in the deposited-protein removing time than in comparative examples 1 to 3.

INDUSTRIAL APPLICABILITY

The bipolar forceps according to the present invention prevent protein from attaching and sticking to the arm tip end portions when used for coagulation, stanching, dissection or similar surgical manipulation in vascular, plastic and general surgical operations, and hence the forceps maintain the original performance and operability and achieve excellent washability.

The invention claimed is:

1. A pair of bipolar forceps provided with a pair of arms which are normally spaced apart at one end and insulated from each other and, when in use, held in contact with each other and supplied with a high-frequency current, wherein opposed surfaces of tip end portions of said pair of arms are each coated with a composite plating film of a noble metal material and nonconductive fine particles, and a laminate plating film of a noble metal material formed on said composite plating film, wherein said fine particles range in particle size from 0.5 µm to 10 µm, the thickness of said composite plating film is in the range of 3 µm to 50 µm, and the thickness of said laminate plating film is in the range of 0.2 µm to 10 µm.

2. The bipolar forceps of claim 1, wherein said noble metal material is at least one kind of metal selected from a group consisting of gold, platinum, silver, palladium, nickel, chromium, copper and tin.

3. The bipolar forceps of claim 2, wherein said nonconductive fine particles consist of a polytetrafluoroethylene or fluorinated ethylene polymer.

4. The bipolar forceps of claim 1, wherein the content of said nonconductive fine particles in said composite plating film is in the range of 0.05 wt % to 20.0 wt %.

5. The bipolar forceps of claim 1, wherein the content of said nonconductive fine particles in said composite plating film is in the range of 4 percent by volume to 50 percent by volume.

* * * * *